United States Patent [19]

Niemann et al.

[11] 4,181,442

[45] Jan. 1, 1980

[54] APPARATUS FOR DETERMINING AMINO ACIDS

[75] Inventors: Ernst-Georg Niemann, Garbsen; Bernd Georgi, Hanover, both of Fed. Rep. of Germany

[73] Assignees: Gesellschaft fur Strahlen- und Umweltforschung mbH, Munchen, Neuherberg, Fed. Rep. of Germany d; Umweltforschung mbH, both of Neuherberg, Fed. Rep. of Germany

[21] Appl. No.: 877,985

[22] Filed: Feb. 15, 1978

Related U.S. Application Data

[62] Division of Ser. No. 799,121, May 20, 1977.

[30] Foreign Application Priority Data

May 20, 1976 [DE] Fed. Rep. of Germany ....... 2622547

[51] Int. Cl.² ........................................... G01N 21/52
[52] U.S. Cl. .................................. 356/417; 250/461 R
[58] Field of Search ................... 250/458, 459, 461 R, 250/461 B; 356/85, 417, 317, 318

[56] References Cited

U.S. PATENT DOCUMENTS

| 3,358,148 | 12/1967 | Conklin et al. | 356/104 |
| 3,498,719 | 3/1970 | Wing et al. | 356/36 |
| 3,941,487 | 3/1976 | Ehret et al. | 356/181 |
| 3,973,849 | 8/1976 | Jackson et al. | 356/97 |
| 4,082,459 | 4/1978 | Wolfe | 356/85 |

OTHER PUBLICATIONS

Merkelo et al., *Science*, vol. 164, Apr. 1969, pp. 301 and 302.
Udenfriend et al., *Science*, vol. 178, Nov. 1972, pp. 871 and 872.
"Fluorometrie, FT-67," a brochure published by the firm Camag Chemie-Erzeugnisse und Adsorptionstecknik AG.

*Primary Examiner*—F. L. Evans
*Attorney, Agent, or Firm*—Spencer & Kaye

[57] ABSTRACT

Apparatus for measuring fluorescence comprises a metal block having a first recess for a sample mount and a second recess for a beam divider. A receiving bore connects both recesses and extends axially from the metal block. A radiation source and an optical focusing device are provided to introduce radiation into the receiving bore. Two exit bores extend from the recesses at an angle, and reflected or fluorescent radiation emitted by the sample and the beam divider pass through the exit bores. Detectors are at the exit bores to measure the radiation.

5 Claims, 3 Drawing Figures

APPARATUS FOR DETERMINING AMINO ACIDS

CROSS REFERENCE TO RELATED APPLICATION

This application is a division of application Ser. No. 799,121, filed May 20, 1977.

BACKGROUND OF THE INVENTION

The present invention relates to an apparatus for the fluorometric determination of amino acids in sugar beets and or sugar refinery products by means of a radiation source, an optical focusing device, a beam divider, a mount for a sample as well as detectors for the fluorescent radiation or reflected radiation, emitted by the sample and the beam divider, respectively.

To determine amino acids (hereinafter called briefly amino-N) in sugar beets and sugar factory products, the photometric ninhydrin method (described by Carruthers et al., Z. Zuckerind. 10, (1960), pages 350 to 354) has been introduced as the official method for sugar factory analysis. The older, simpler blue number method (described by V. Stanek, P. Z. Zuckerind. csl. Rep. 59, (1934), pages 129 to 142), which is based on the formation of chelate-like deeply blue colored $Cu^{2+}$ amino acid complexes, was additional recommended for the automatic determination of amino-N in sugar beets, in spite of its drawbacks. An alternative method for automatic determination of amino-N in sugar beets is not available in the prior art. The blue number method compiles the α-amino-N content of the amino acids and amides. γ-amino butyric acid and betaine do not react in the blue number method and cannot be determined by the blue number method.

The significant drawbacks of the blue number method are its low sensitivity, its high blind value, and its susceptibility are its low sensitivity, its high blind value, and its susceptibility to clouding ($PbCO_3$) and colorations in the analysis medium. The clouding and colorations result predominantly from a pretreatment with a contaminating lead acetate filter.

The ninhydrin method also has the drawbacks of being a sensitive reagent, requiring time-consuming heating and being subject to interference from ammonia. It is, therefore, unsuitable for automation.

It is known in the art (Science, Vol. 178, pp. 871 and 872, German Offenlegungsschrift No. 2,102,985) to make fluorometric determinations of amino acids in amino acid containing samples.

Further, "Fluorometrie, FT-67," a brochure published by the firm Camag Chemie-Erzeugnisse und Adsorptionstechnik AG, describes a fluorometer in which the measuring beam from the sample, excited by a filtered primary beam from an UV radiation source and a comparison beam from the radiation source alternatingly impinge via a diffusing mirror on a detector. The fluorescence intensity is measured in this optical bridge by intensity matching of measuring and comparison beam.

A fluorometer of the above-mentioned type, as described in Science, Vol. 164, 1969, pages 301 and 302, employs an He-Ne laser at 632.8 nm to excite fluorescence in the sample. However, the determination of amino acids requires wavelengths in the range of less than 410 nm. For this wavelength range there do not exist any continuously operating lasers. Moreover, the individual elements of the fluorometer are again neither thermally nor mechanically coupled together.

SUMMARY OF THE INVENTION

It is an object of the present invention to provide an apparatus for performing fluorescence measurements.

Another object is to provide apparatus for practicing a fluorometric method for determining amino acids.

A further object is to provide such apparatus which is distinguished by its accuracy and an increase in detection sensitivity for amino acid contents while eliminating mechanical, thermal and optical interference effects.

Additional objects and advantages of the present invention will be set forth in part in the description which follows and in part will be obvious from the description or can be learned by practice of the invention. The objects and advantages are achieved by means of the processes, instrumentalities and combinations particularly pointed out in the appended claims.

To achieve the foregoing objects and in accordance with its purpose, as embodied and broadly described, the present invention provides a particularly advantageous apparatus for practicing a fluorometric method. This apparatus is distinguished by its accuracy and its 50 to 400 fold increase of the detection limits and permits constant automatic measurements of the fluorescing complexes, even in flow-through operation. The apparatus of the present invention comprises: a metal block having a first recess for a sample mount and a second recess for a beam divider; a receiving bore connecting both recesses and extending axially from the metal block; a radiation source and an optical focusing device to introduce radiation into the receiving bore; a first exit bore extending at an angle from the first recess and through which can pass fluorescent radiation emitted by a sample in the sample mount; a second exit bore extending at an angle from the second recess and through which can pass reflected radiation from the beam divider; a detector at the first exit bore for detecting fluorescent radiation; and a second detector at the second exit bore for detecting reflected radiation.

In a preferred embodiment of the apparatus, a condensor stray light trap is provided in the first exit bore and a filter is provided in the first exit bore between the sample mount and the first detector. Preferably, the receiving bore is terminated by means of an interference filter.

In order to be able to correct or prevent, respectively, bleaching effects, it is of particular advantage that the excitation energy of the radiation source is variable.

It is to be understood that both the foregoing general description and the following detailed description are exemplary, but are not restrictive of the invention.

BRIEF DESCRIPTION OF THE DRAWINGS

The accompanying drawings, in which like numbers indicate like parts, illustrate examples of presently preferred embodiments of the invention and, together with the description, serve to explain the principles of the invention.

Of the drawings.

DETAILED DESCRIPTION OF THE INVENTION

Figure 1:
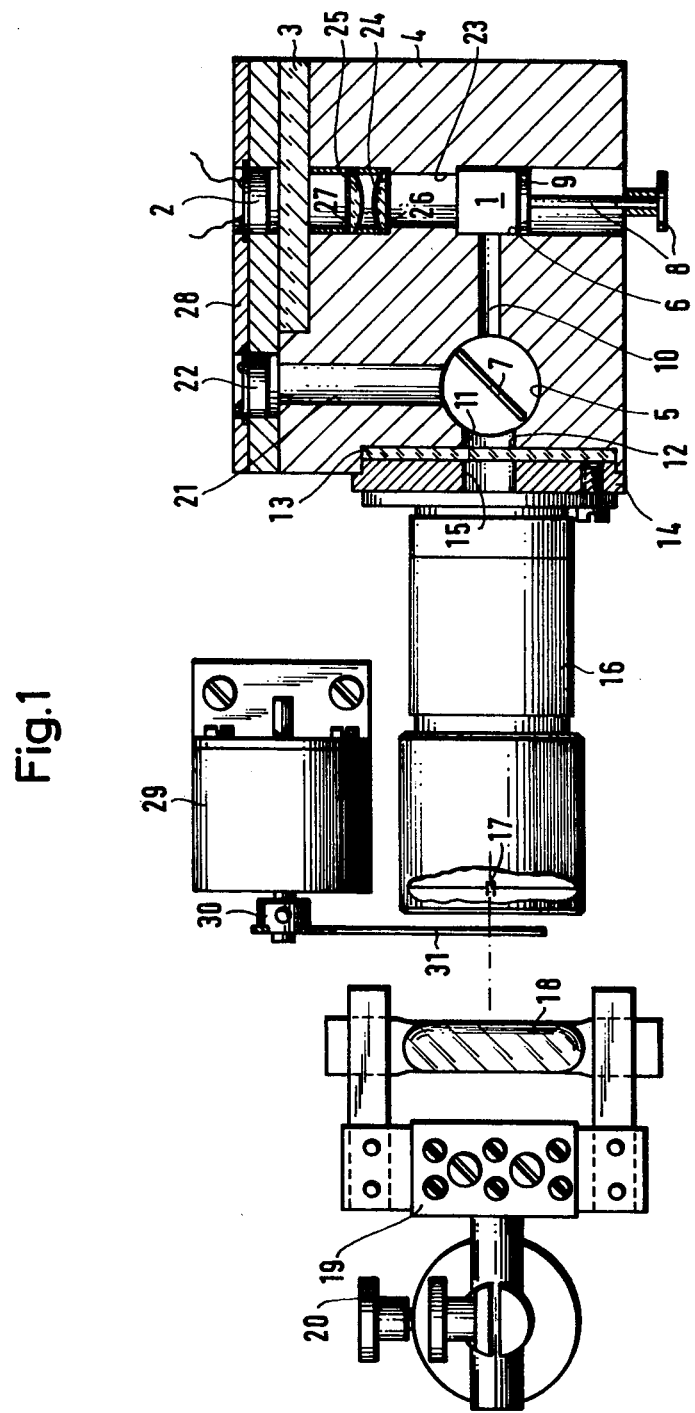
FIGS. 1 to 3 show one embodiment of an apparatus made in accordance with the teachings of the present invention.

The apparatus of the present invention can be used to practice a fluorescamine method.

The basis of the fluorescamine method is the binary reaction of the nonfluorescent fluorescamine (I) with amino acids (II) to produce a fluorescent substance (III). This binary reaction generally is performed using an excess of the nonfluorescent fluorescamine and, during the reaction, a complete hydrolysis of the excess fluorescamine occurs resulting in the production of nonfluorescent water-soluble products.

The reaction with fluorescamine takes place almost quantitatively in aqueous solution at room temperature within fractions of a second, and generally has an optimum pH between pH 8 and 10. Rapid intensive mixing of the fluorescamine reagent and sample solution containing the amino acids is absolutely necessary due to the hydrolysis of fluorescamine, which hydrolysis is a competing reaction to the formation of the fluorescent substance. At room temperature, the fluorescamine reagent is stable for at least 2 weeks in acetone not containing any water. Secondary amino acids, such as, for example, proline or hydroxyproline, do not react with fluorescamine, but are of subordinate significance in sugar beets. In contrast to the ninhydrin method, ammonia does not interfere in the fluorescamine method, since the resulting colored fluorescent substance has a fluorescence intensity which is about 1000 times lower than that obtained in the ninhydrin method.

The apparatus of the present invention can be used in the fluorescamine method to determine amino acids in substances which do not contain lead salts or lead filtrates, such as syrups and molasses products, and can be used to determine amino acids in lead acetate filtrates of sugar beets. A critical step in the use of the fluorescamine method on lead acetate filtrates of sugar beets is the selection of a suitable buffer substance which, among other things, must not produce a precipitation in alkali solution with $Pb^{2+}$ ions so that the use of buffer mixtures usually employed at pH above pH 7, such as, for example, borate, phosphate, tris and others, cannot be employed in the fluorescamin method of the present invention when lead salts or lead filtrates are present. These difficulties can be overcome by the selection of a buffer from the series of the N-substituted glycines, such as, for example, bicine, which has the chemical name N,N-bis(2-hydroxyethyl)-glycine. Bicine has a $pK_A$ of 8.35 at 20° C. and a $\Delta pK_A/°$ C. of $-0.018$. Thus, by selecting an appropriate buffer for use in the fluorescamine method as applied to substances which contain lead salts or lead filtrates, one of the most important method requirements is met so that fluorescamine can be used not only for the analysis of syrups and molasses, but also for routine determinations of amino-N of sugar beets. Instead of Bicine, Tricine can be used however with a reduced quantum efficiency.

All samples are measured against the reagent blind value (water instead of sample solution). With exception, the sample blind value can be neglected in sugars.

Figure 2:
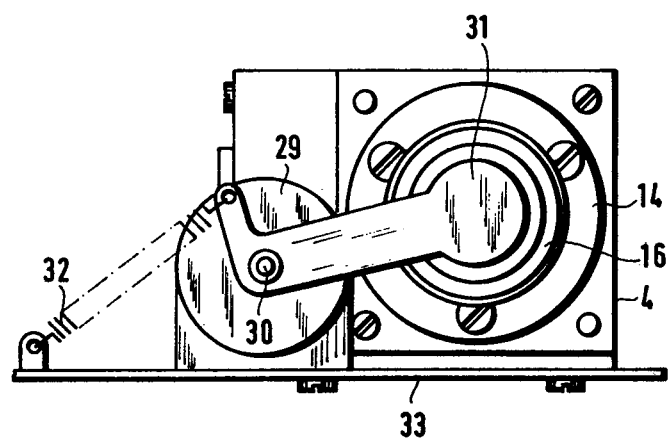
Figure 3:
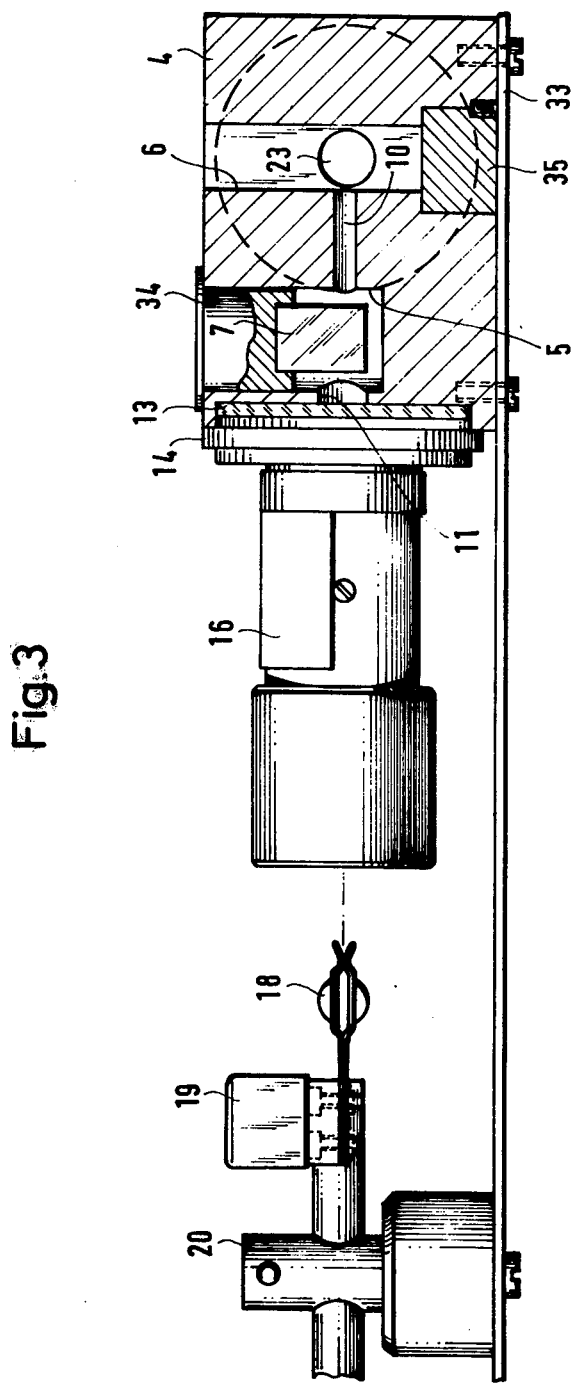

Turning now to FIGS. 1 to 3, there is shown apparatus with which the fluorescence measurement can be made. The apparatus is a dual beam device with which it is possible to compensate for fluctuations in light intensity. It can also be used to effect a controlled connection between excitation and measuring as well as to prevent bleaching effects.

FIG. 1 shows a top view, partially in section, of the fluorometer according to the present invention. The fluorometer comprises a metal block 4, e.g., of aluminum, in which two recesses 5 and 6 are provided in a direction perpendicular to the plane of the drawing, i.e., in vertical direction. A beam divider 7, seen also in FIG. 3, is accommodated in recess 5, while in recess 6 a sample mount in the form of a flowthrough cuvette 1 is held by means of a clamping device 8 and a plunger 9. Both recesses 5 and 6 are connected together via a common receiving bore, generally 10. Bore 10 contains an axially continuing bore section 11 which starts at recess 5 and extends to the surface of metal block 4. The exit opening 12 of bore section 11 is closed by an interference filter 13 as well as by a mounting plate 14 having a coaxial entrance opening 15. A focusing device 16 (Kohler illumination) is screwed to mounting plate 14 and is provided with an aperture 17 against the outside.

A radiation source 18 comprising a quartz burner and a mount 19 and 20 generates radiation with an excitation energy which is variable between 30 and 70 watts. The light emanating from this quartz burner 18 passes through aperture 17 into focusing device 16 and is there formed into a parallel light beam and filtered by interference filter 13. Depending on the type of coloring agent employed, interference filter 13 permits light to pass of an excitation energy of 408 nm or 367 nm, respectively. This light then impinges on beam divider 7. Beam divider 7 is in the form of a wafer of glass and reflects about 10% of this light into an exit bore 21, which extends perpendicularly to the impinging light beam. Here it impinges on a photoelement 22 and is recorded. Approximately 10% of the light is always reflected by beam divider 7.

The remaining 90% of the light passes through common receiving bore 10 and impinges on the flowthrough cuvette 1 and the sample contained therein. In the sample, the impinging light excites the sample and causes the sample to emit fluorescent light which is cut out by an exit bore 23. Exit bore 23 is at an angle of 90° to the direction of impingement of the exciting radiation. A condensor and stray light trap which includes lenses 24 and 25 and apertures 26 and 27 is disposed in exit bore 23 and produces parallel beams of fluorescent light. This fluorescent light passes through a filter 3 which passes, depending on the coloring agent, radiation above 470 nm or 450 nm, respectively. This filtered light impinges on a further photoelement 2. The value measured in the photoelement 2 is compared with the value measured by photoelement 22, either by a quotient or difference measurement. The two photoelements 2 and 22 are held at metal block 4 by means of a plate 28.

A rotary magnet 29 which has an aperture 31 disposed at its axis of rotation 30 serves to control the exciting irradiation period or synchronize the entry radiation with the measurement, respectively, i.e., adapt them to one another.

FIG. 2 is a view of the fluorescence device showing rotary magnet 29 with axis 30 and aperture 31. Aperture 31 is designed as a lever arm on which acts a reset spring 32. Rotary magnet 29 as well as reset spring 32 and metal block 4 are fastened to a common base plate 33. Also visible in FIG. 11 is locking plate 14 as well as the front end of focusing device 16.

FIG. 3 is a vertical sectional view of metal block 4. It shows an entrance opening where exit bore 23 meets with recess 6. FIG. 12 further shows the common bore 10 and recess 5. Beam divider 7 is held by a plug 34, which simultaneously seals recess 5 from the outside. Filter 13 is also shown with which bore 11 is closed. The focusing device 16 is screwed to plate 14. Moreover, recess 6 is closed at the bottom by means of a further plug 35.

It will be understood that the above description of the present invention is susceptible to various modifications, changes and adaptations and the same are intended to be comprehended within the meaning and range of equivalents of the appended claims.

What is claimed is:

1. Apparatus for measuring fluorescence comprising
    (a) a metal block having a first recess for a sample mount and a second recess for a beam divider;
    (b) a receiving bore connecting both recesses and extending axially from the metal block;
    (c) a radiation source and an optical focusing device to introduce radiation into the receiving bore;
    (d) a first exit bore extending at an angle from the first recess and through which can pass fluorescent radiation emitted by a sample in the sample mount;
    (e) a second exit bore extending at an angle from the second recess and through which can pass radiation reflected by the beam divider;
    (f) a first detector at the first exit bore for detecting fluorescent radiation; and
    (g) a second detector at the second exit bore for detecting reflected radiation.

2. Apparatus as defined in claim 1 wherein a condensor stray light trap is provided in the first exit bore and a filter is provided in the first exit bore between the sample mount and the first detector.

3. Apparatus as defined in claim 1 wherein the receiving bore is terminated by means of an interference filter.

4. Apparatus as defined in claim 1 wherein the excitation energy of the radiation source is variable.

5. Apparatus as defined in claim 1 wherein the beam divider comprises an obliquely arranged glass plate.

* * * * *